United States Patent [19]

Daniell, Jr.

[11] 4,233,967
[45] Nov. 18, 1980

[54] CUSTOM-FITTED KNEE GUARD AND BRACE

[76] Inventor: Roy B. Daniell, Jr., 2026 "B" Tycoon Rd., Chamblee, Ga. 30341

[21] Appl. No.: 896,990

[22] Filed: Apr. 17, 1978

[51] Int. Cl.³ .............................................. A61F 5/00
[52] U.S. Cl. .................................. 128/80 C; 128/165; 128/87 R; 128/90
[58] Field of Search ...................... 128/80 L, 90, 80 F, 128/87 R, 820, 165, 88, DIG. 15; 2/222

[56] References Cited

U.S. PATENT DOCUMENTS

| 3,779,654 | 12/1973 | Horne | 128/80 C |
| 3,799,158 | 3/1974 | Gardner | 128/80 C |
| 3,817,244 | 6/1974 | Taylor | 128/80 C |
| 3,906,943 | 9/1975 | Arlock | 128/89 R |
| 3,958,569 | 5/1976 | Vosburgh | 128/80 C |

OTHER PUBLICATIONS

The "Nature and Properties of Engineering Materials", 2nd Edition Zbigniew D. Jastrzebski, John Wiley & Sons, New York, 1976, Chart A4, Structures and Properties of Thermoplastics.

*Primary Examiner*—Robert W. Michell
*Assistant Examiner*—J. L. Kruter
*Attorney, Agent, or Firm*—Vivian L. Leon; Harry I. Leon

[57] ABSTRACT

A knee guard and brace having semi-rigid thigh and calf encasements for the protection of the knee area from the thigh to the calf. The device, other than padding, is made entirely of a plastic material. The brace is lightweight and designed for unusual strength by using an arch at the joint, covering the side of the knee, and a recess in each of the longitudinal support ribs which run parallel to the leg, the recessed portions of the ribs being embodied in the calf and thigh encasements. The encasements are secured to a wearer's leg by straps which are also part of the molding. The straps are perforated to seat over studs which are molded in the encasements. The straps and encasements are molded again at a low temperature to the contour of a user's legs.

2 Claims, 6 Drawing Figures

CUSTOM-FITTED KNEE GUARD AND BRACE

BACKGROUND OF THE INVENTION

1. Field of the Invention

The present disclosure relates generally to knee guards and braces and more particularly to such devices for reducing the chance of injury and the extent of damage to the knee area which an athlete may incur during contact sports and to give aid and support in the rehabilitation of such injury.

2. Description of the Prior Art

The principal injury to the leg develops from a blow to or a twist in th knee area. An obvious solution to protect an athlete's knee from the blow type injury would seem to be, to apply a strong metal apparatus to withstand the shock of such a blow. Of the many knee braces made, that is exactly what has been done. However, this solution has many problems. The metal knee braces of the prior art are heavy, bulky, time-consuming to affix, uncomfortable to wear, and short-lived. Their bulkiness causes a loss of mobility in a wearer's leg; their weight contributes to their tendency to slide down the leg. To prevent these braces from sliding doen when the athlete is running, excessive binding with strapping is necessary. Affixing these braces—adjusting and securing them to a wearer's leg—is very time-consuming. Moreover, there is discomfort to the wearer from the wrappings which cause perspiration to increase the weight and irritate the skin. The corrosive effect of perspiration and dust on the metal joints themselves, whether ball bearing or otherwise, of these braces causes the joints to be short-lived. Because of these inherent problems, athletes are forced to wear these braces only after an injury to a leg and not before such injury.

The lightweight braces of the prior art, on the other hand, by and large are tubes of elastic with longitudinal strips of plastic or thin metal for support on both sides of the knee. They were not designed to withstand a strong lateral blow or a twisting of the knee, but were designed as a support in a therapeutic manner.

SUMMARY OF THE INVENTION

The present invention contemplates a knee guard and brace comprising a pair of side members molded of a thermoplastic material. One of the side members is adapted to fit on the inside of a wearer's leg and the other on the outside of the leg. Each side member is attached to the wearer's thigh and calf and held in place relative to the other member by means of straps. The straps extend laterally around the leg from flanges on the outside member and have a plurality of equally spaced holes so that the straps can be seated on studs attached to flanges on both side members. The semi-rigid flanges can be further molded at low temperature to conform to the contour of the individual's legs. With the flanges so molded, the leg guard and brace becomes a lightweight, custom-fitted, semi-rigid and supportive encasement which inhibits torsional twisting of the leg.

Each side member has two pivotally-connected ribs which together longitudinally span the area of the knee joint at the side of the knee cap and form an arch over this area. The arch is entirely disposed laterally from the surface of the area. The force of a blow to this arch tends to be dissipated to the large muscles of a wearer's thigh and calf rather than absorbed by the knee joint. Opposite sides of the ribs are flanged above and below the knee area. In order to reduce further the weight of the knee guard and brace, a recess is formed in each rib, this recess being disposed within the flanged portion of each rib and contiguous to the wearer's skin.

Thus the present invention provides a lightweight, but extremely strong and less cumbersome knee guard and brace which can be used by most athletes participating in contact sports to reduce the chance of injuries from side or lateral blows to the legs and torsional twisting of the knees.

A further object of this invention is to provide a lightweight, but strong supportive and protective apparatus for use by orthopedic patients in need of knee or leg bracing.

Other objects and advantages will appear from the following description of an example of the invention, when considered in connection with the accompanying drawing, and the novel features will be particularly pointed out in the appended claims.

BRIEF DESCRIPTION OF THE DRAWINGS

My invention is disclosed in two modifications shown in the accompanying drawings.

DESCRIPTION OF THE INVENTION

This knee guard and brace is virtually completely molded of plastic by an injection molding process. By the use of injection molding, all the necessary parts, fastenings, straps, load bearing longitudinal support ribs, joints and encasements are made integrally into one piece. In essence, there are actually only four parts to each knee guard except the snap rings as will hereinafter become apparent.

Figure 2:
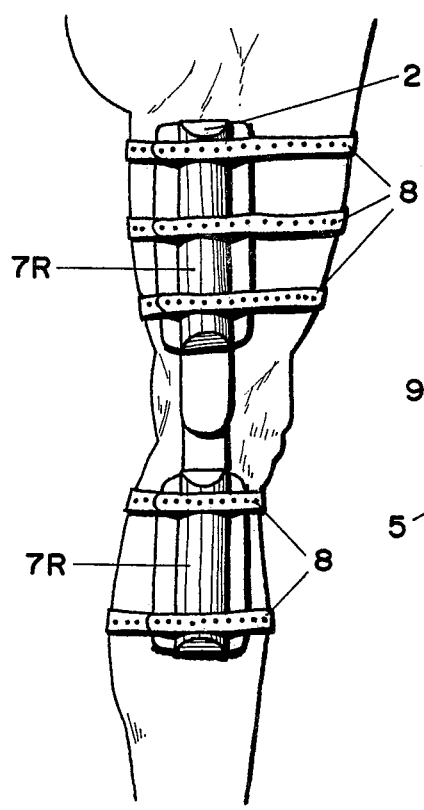
FIGS. 2 and 3 are perspective views of a knee guard and brace incorporating the present invention attached to right leg of a wearer. A detail of the joint area in FIG. 3 shows an enlargement of the pin on the end of a longitudinal support rib and of a cross-section of the longitudinal support rib into which the pin is inserted and held in place by a snap ring.
Figure 3:
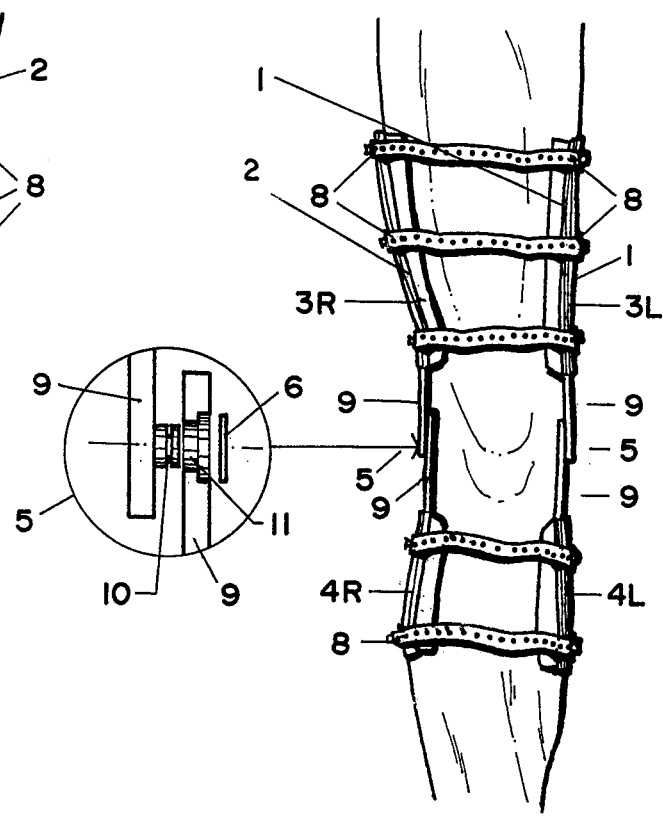

Referring to FIGS. 2 and 3 of the drawing, the knee guard and brace is comprised of two side members, an inside member 1 for the inside support of the leg and an outside member 2 for the outside support. Each of the side members are of two parts; the inside support member has a lower thigh support member 3L and an upper calf support member 4L; likewise, the outside member has a pair of thigh and calf support members 3R and 4R. Each pair of support members is held together at the joint 5 by a snap ring 6.

Figure 1:
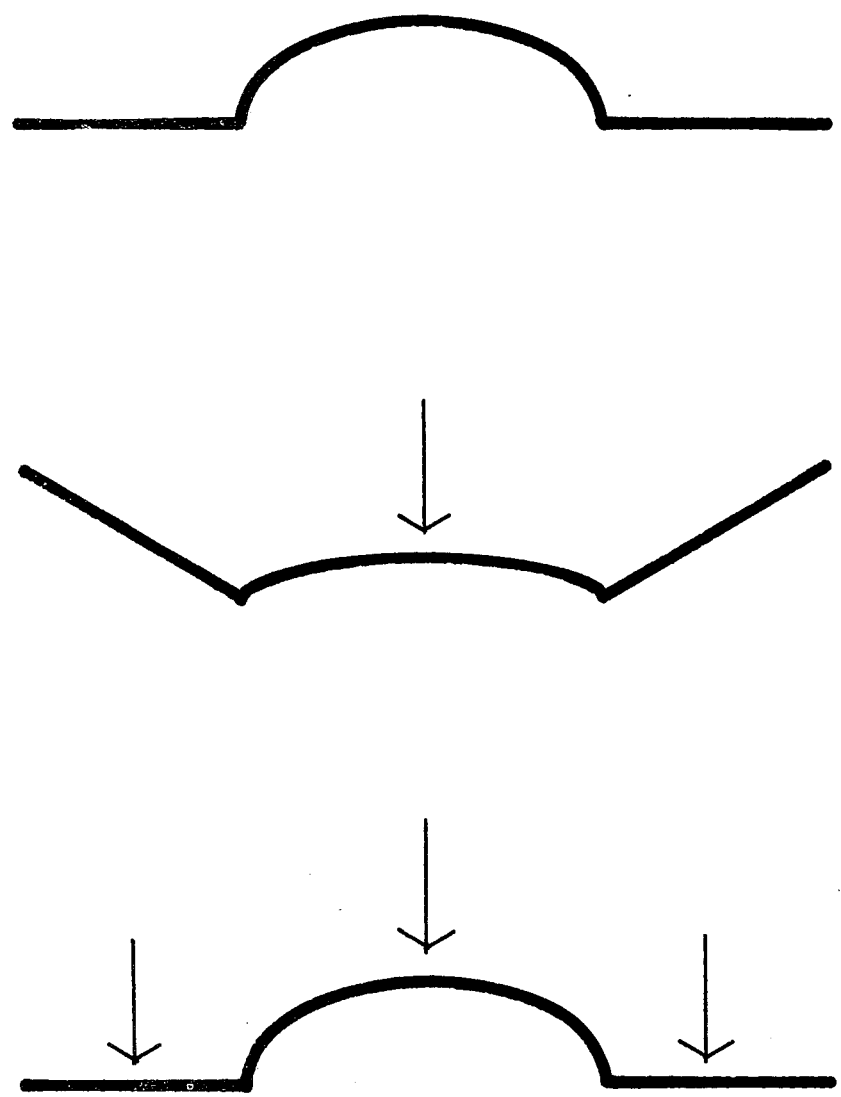
FIG. 1 shows the principle which this knee guard and brace utilizes to protect the knee from a lateral blow.

To protect the knee from a side or lateral blow an arch is used. FIG. 1 illustrates the principle by which an arch strengthens the knee guard and brace. In the top illustration of FIG. 1, an arch connecting two levers is shown schematically; the levers are represented by straight lines. As a force, shown as an arrow in the second illustration of FIG. 1, is applied to the arch, the ends of the levers distant from the arch are displaced upward. Now if another force, represented by the two outer arrows in the bottom illustration of FIG. 1, is applied to the levers, the blow to the arch is resisted or not allowed to penetrate to the area under the arch.

The arch in the knee guard and brace comprises the joint 5 and the sections 9 on either side of the joint. The levers are longitudinal support ribs 7R which run parallel to the leg in the thigh and calf support members. The forces on the levers are the straps 8. The arch can be molded to conform with a wearer's leg by heating and bending the flat sections 9 between the joint 5 and the flanged portions of the thigh and calf support members.

Without the arch in the knee guard and brace, whenever a blow, whether transmitted by a foot, head or shoulder, strikes the knee, the entire force is concentrated into a few square inches directly on the weakest and most vulnerable area of the leg structure. With the arch in the knee guard and brace, the power of the blow is distributed to the upper and lower leg sections which are the strongest.

When the leg is in the bending position, while running, and the blow is received laterally from the outside, the inside member 1 of the knee guard and brace is taut against the knee, reducing the chance of collapse. The inside member 1 is held taut against the knee by a plurality of straps 8 binding it to the outside member 2.

Torsional injury to the knee is reduced with the knee guard and brace by restricting the knee to bend only in the same plane as the knee guard and brace.

The outer skin of the knee guard and brace, excluding the joint area, is wafer thin. During a molding process, the outside support members are shaped to the wearer's thigh and calf contours. The molding for shaping to the leg contour is simply performed by heating the wafer thin plastic therein to a pliable state, approximately 300°, and placing the support members over a heat-protected leg, and allowing the plastic therein to form quickly and to cool quickly. The molded outside member 2 is then secured by the straps 8 to the inside member 1. The straps 8 are also contour molded to the wearer's leg. Once the plastic material becomes semi-rigid, the knee guard and brace encases the wearer's leg resisting unnecessary torsional movement.

Structural strength as well as weight reduction in the portions of the longitudinal support ribs 9 in the upper and lower leg pieces, 3-4, extending roughly from the ends of the arch in both directions parallel to the leg is accomplished by the use of arching and honeycombing. By making the outer skin of the knee guard and brace, excluding joint area, is wafer thin, less than 1/16 inch, additional weight reduction is obtained. Further weight reduction is made by perforation without unnecessary loss of strength.

As seen in the detail of FIG. 3, the joint 5 comprises a simple dowel pin 10 molded integrally with one of the ribs and inserted into a hole 11 of the same diameter as the pin 10 and which is molded integrally in the overlapping rib. With the dowel pin protruding from the hole 11, a retaining snap ring 6 is secured around the protrusion; and the joint is complete and strong. While joints of most braces are heavy and bulky and have problems from rust or because of bearings, the joint 5, being formed of a noncorrosive plastic, is lightweight and long lasting, requiring little maintenance.

MODIFICATION

Figures 4, 5, 6:
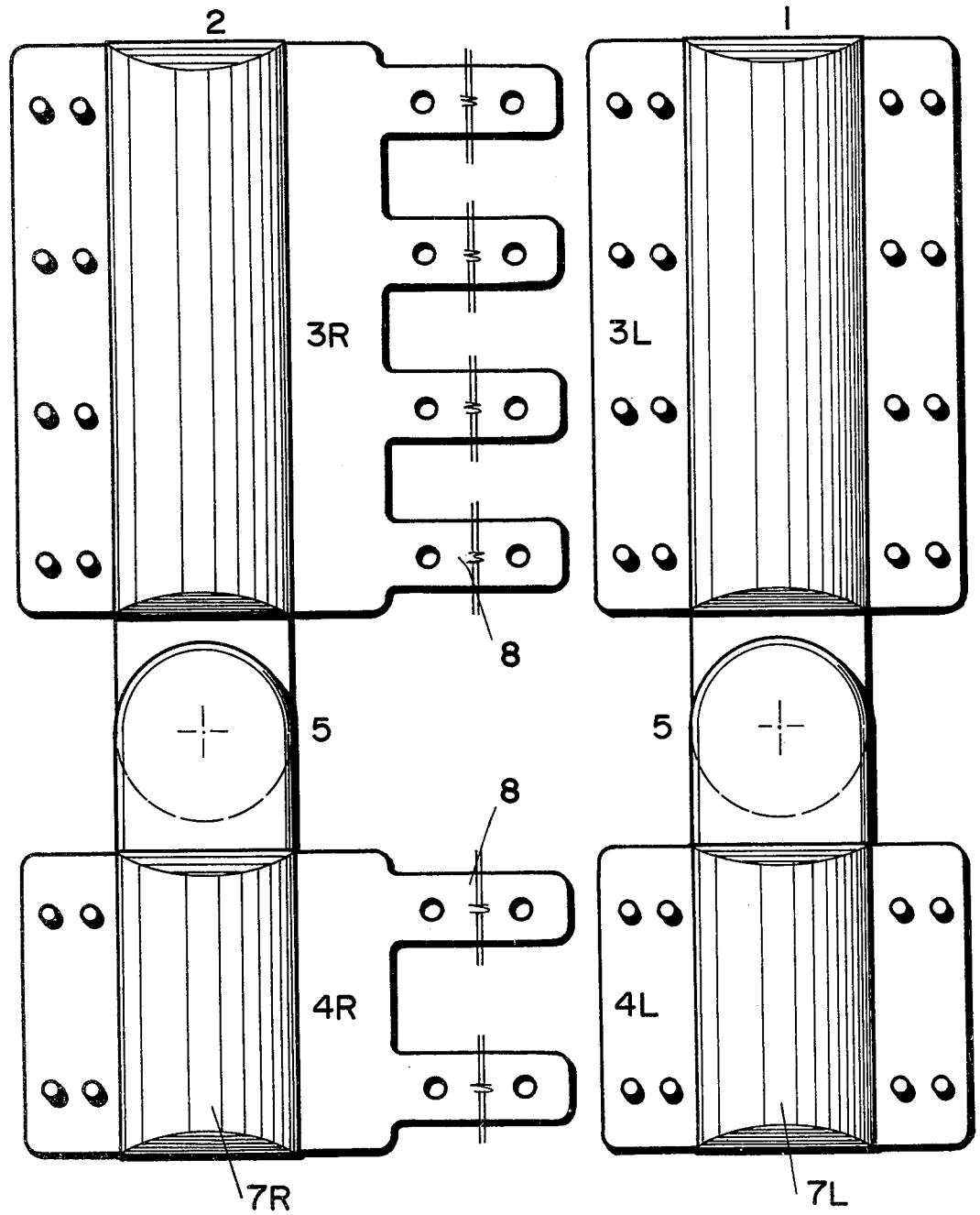
FIGS. 4 and 6 are the frontal elevational and end views, respectively, of an alternative embodiment of the outside member of a knee guard and brace for the right leg according to the present invention.
FIG. 5 is a frontal elevational view of the alternative embodiment seen in FIGS. 4 and 6 for the inside member of a knee guard and brace.

Both the embodiment of the present invention seen in FIGS. 2 and 3 and the embodiment seen in FIGS. 4-6 have a plurality of straps 8 each of which have a plurality of holes. The holes are formed in the straps by any appropriate means such as perforation or molding. The straps 8 are provided to connect the flanges of the lower thigh support members 3R and 3L to each other and the flanges of the upper calf support members 4R and 4L to each other.

In the alternative embodiment seen in FIGS. 4-6, the straps 8 are lateral extensions of portions of the flanges of the outside member 2; and a set of straps together with a flange comprise a single, unitary, one-piece article made entirely of a plastic material. Moreover, a plurality of studs which are attached to the flanges of both the inside and outside members 1 and 2 are provided for securing the knee guard and brace to a wearer's leg. In use, the studs are aligned with an equal number of holes in the straps when they are wrapped around a wearer's leg and seated over the studs. The studs which may be molded or riveted to the flanges have the same diameter at the interface between the studs and the flanges as the diameter of the holes. When the flanges and straps are molded to th contours of a wearer's leg by the molding process described hereinbefore, the knee guard and brace provides a custom-fitted, semi-rigid encasement which resists torsional twisting of a wearer's leg.

Furthermore, as is best seen in FIG. 6, a recess is provided in a portion of each rib in the alternative embodiment. This recess is contiguous to the wearer's skin and is disposed within the portion of each rib from which the flanges extend laterally. These recesses significantly reduce the overall weight of the knee guard and brace.

It will be understood that various changes in the details, materials, and arrangement of parts, which have been herein described and illustrated in order to explain the nature of the invention, may be made by those skilled in the art within the principle and scope of the invention as expressed in the appended claims. What is claimed is:

1. A knee guard and brace, which comprises: inside and outside members which are adapted to fit on the inner and outer sides, respectively, of a wearer's leg, each side member comprising a pair of thigh and calf support members; each support member having a rib which runs parallel to the wearer's leg from the knee joint to substantially the distal edges of the support member; means pivotally interconnecting the end portions of the ribs in overlapping engagement; each support member having a pair of semi-rigid flanges which extend laterally from opposite sides of the rib, the flanges being wholly disposed within the portions of the thigh and calf support members which are located above and below the segments of the knee joint at the sides of the knee cap, respectively; a section of each rib disposed between the overlapping end portions and the proximate edges of the flanges being curved, the radius of curvature of the section being such that an arch is formed which longitudinally spans the area of the knee joint at the side of the knee cap when the end portions are interconnected in overlapping engagement, the arch being entirely disposed laterally from the surface of the knee, so that the force of a blow upon the knee guard and brace received at the knee joint tends to be dissipated to the large muscles of the wearer's thigh and calf rather than absorbed by the knee joint; the flanges of the outside member having a plurality of laterally extending straps connecting the upper flanges to each other and the lower flanges to each other, portions of the straps being contiguous with the flanges, the straps having a plurality of equally spaced holes; a plurality of studs attached to the flanges of both the inside and outside members, the studs being aligned with an equal number of holes in the contiguous portions of the straps, and the studs having the same diameter at the interface between the studs and the flanges are the diameter of the holes, so that the straps can be seated over the studs, securing the knee guard and brace and encasing a wearer's leg above and below the knee; the support members being constructed of a thermoplastic material which becomes pliable, upon heating, at temperatures which are sufficiently low that the flanges can be shaped to the contour of a heat protected leg, thereby enabling the knee guard and brace to form a custom-fitted, simi-rigid encasement which inhibits torsional twisting of the leg.

2. A knee guard and brace, which comprises: inside and outside members which are adapted to fit on the inner and outer sides, respectively, of a wearer's leg, each side member comprising a pair of thigh and calf support members; each support member having a rib which runs parllel to the wearer's leg from the knee joint to substantially the distal edges of the support members; means pivotally interconnecting the end portions of the ribs in overlapping engagement; each support member having a pair of semi-rigid flanges which extend laterally from opposite sides of the rib, the flanges being wholly disposed within the portions of the thigh and calf support members which are located above and below the segments of the knee joint at the sides of the knee cap, respectively; a section of each rib disposed between the overlapping end portions and the proximate edges of the flanges being curved, the radius of curvature of the section being such that an arch is formed which longitudinally spans the area of the knee joint at the side of the knee cap when the end portions are interconnected in overlapping engagement, the arch being entirely disposed laterally from the surface of the knee, so that the force of a blow upon the knee guard and brace received at the knee joint tends to be dissipated to the large muscles of a wearer's thigh and calf rather than absorbed by the knee joint; each rib forming a recess contiguous to the wearer's skin, the recess being wholly disposed within the portion of each rib from which the flanges extend laterally; the flanges of the outside member having a plurality of laterally extending straps, the straps connecting the upper flanges to each other and the lower flanges to each other, portions of the straps being contiguous with the flanges so that the knee guard and brace encases wearer's leg above and below the knee; the support members being constructed of a thermoplastic material which becomes pliable, upon heating, at temperatures which are sufficiently low that the flanges can be shaped to the contour of a heat protected leg, thereby enabling the knee guard and brace to form a custom-fitted, semi-rigid, lightweight encasement which inhibits torsional twisting of the leg.

* * * * *